US011589946B2

(12) United States Patent
Hofberger et al.

(10) Patent No.: US 11,589,946 B2
(45) Date of Patent: Feb. 28, 2023

(54) HEAD-HOLDER SUPPORT

(71) Applicant: Brainlab AG, Munich (DE)

(72) Inventors: Stefan Hofberger, Munich (DE); Wolfgang Steinle, Munich (DE); Nils Frielinghaus, Heimstetten (DE)

(73) Assignee: Brainlab AG, Munich (DE)

( * ) Notice: Subject to any disclaimer, the term of this patent is extended or adjusted under 35 U.S.C. 154(b) by 652 days.

(21) Appl. No.: 16/603,291

(22) PCT Filed: Sep. 7, 2018

(86) PCT No.: PCT/EP2018/074100
§ 371 (c)(1),
(2) Date: Oct. 7, 2019

(87) PCT Pub. No.: WO2020/048608
PCT Pub. Date: Mar. 12, 2020

(65) Prior Publication Data
US 2021/0220073 A1     Jul. 22, 2021

(51) Int. Cl.
| | | |
|---|---|---|
| *A61G 15/00* | (2006.01) | |
| *A61B 90/14* | (2016.01) | |
| *A61B 34/30* | (2016.01) | |
| *A61G 13/10* | (2006.01) | |
| *A61G 13/12* | (2006.01) | |
| *A61B 90/50* | (2016.01) | |
| *A61B 17/00* | (2006.01) | |

(52) U.S. Cl.
CPC .............. *A61B 90/14* (2016.02); *A61B 34/30* (2016.02); *A61G 13/101* (2013.01); *A61G 13/121* (2013.01); *A61B 2017/0092* (2013.01); *A61B 2090/508* (2016.02)

(58) Field of Classification Search
CPC ........ F16M 13/02; A61B 90/14; A61B 34/30; A61G 13/101; A61G 13/121
USPC ......................................................... 128/845
See application file for complete search history.

(56) References Cited

U.S. PATENT DOCUMENTS

2017/0325906 A1\* 11/2017 Piecuch ................. A61B 34/20
2018/0132965 A1\* 5/2018 Nahum ................. A61B 90/14

FOREIGN PATENT DOCUMENTS

| EP | 3284434 A1 | 2/2018 |
|---|---|---|
| WO | 2011018100 A1 | 2/2011 |

OTHER PUBLICATIONS

International Search Report and Written Opinion for corresponding international application No. PCT/EP2018/074100, dated May 31, 2019. 13 Pages.

\* cited by examiner

*Primary Examiner* — Todd M Epps
(74) *Attorney, Agent, or Firm* — Tucker Ellis LLP

(57) ABSTRACT

A head-holder support for attaching a medical head-holder to a patient table is provided that has a rigid base body, an adjustable and lockable head-holder interface at the base body, which is adapted to adjustably couple the head-holder to the base body by providing at least three degrees of freedom for the spatial relative position between the head-holder and the base body, wherein the at least three degrees of freedom are lockable so as to establish a rigid coupling between the head-holder and the base body, and at least one robotic arm interface at the base body, which is adapted to provide a rigid coupling between a robotic arm and the base body.

19 Claims, 7 Drawing Sheets

HEAD-HOLDER SUPPORT

RELATED APPLICATION DATA

This application is a national phase application of International Application No. PCT/EP2018/074100 filed 7 Sep. 2018, the contents of which are incorporated herein by reference.

FIELD OF THE INVENTION

The present invention relates to a head-holder support for attaching a medical head-holder to a patient table such that a patient's head is immobilized for medical robotic procedures performed on or next to the patient's head.

TECHNICAL BACKGROUND

In order to immobilize a patient's head during medical procedures such as brain-, ear-nose-throat-(ENT-), craniomaxillofacial-(CMF-) or cervical-spine-surgery, so-called head-holders or stereotactic frames are commonly used. Such head-holders are often coupled to the surgical table the patient rests on and may comprise at least three pins held by a substantially U-shaped frame with an adjustable width between the frame-legs, such that the pins penetrate the patient's scalp and engage the patient's cranial bone when the legs of the U-shaped frame are moved towards each other.

For assisting in medical procedures, robotic or semi-robotic setups have been used more and more often in recent time, which of course need to be securely fastened with respect to the patient's anatomy the procedure is performed on, for example the patient's head.

Such setups may for example hold instruments in place or may define trajectories for introducing an instrument into the patient's anatomy.

In order to meet the above outline requirements, US 2017/0325906 A1 suggests a U-shaped head-holder-frame that also carries a robotic support structure. Solutions of this kind however cumbersome to handle and often come with a limited working area for the robotic support structure, since the head-holder's U-shaped frame generally defines the positional arrangement of the support structure with respect to the patient.

A different approach is followed by stand-alone systems that include a head-holder and a robotic arm, both of which are secured to the ground and via common frame. Such ground-supported setups however demand a large footprint in the operating theater and are therefore rather obstructive for medical personnel.

The present invention has the object of providing a support structure for a medical head-holder which not only provides a secure fixation of the patient's head during surgery, but also allows for a secure fixation of a robotic or semi-robotic installation with respect to the patient's head.

The present invention can be well used for any medical procedures performed on the patient's head or vicinity thereof and require a secure fixation of the patient's head. To this end, the present invention can be used together with medical installations and systems such as Airo®, Cirq®, both products of Brainlab AG.

Aspects of the present invention, examples and exemplary steps and their embodiments are disclosed in the following. Different exemplary features of the invention can be combined in accordance with the invention wherever technically expedient and feasible.

GENERAL DESCRIPTION OF THE INVENTION

In general, the invention reaches the aforementioned object by providing, in a first aspect, a head-holder support for attaching a medical head-holder to a patient table, having a rigid base body and a mounting device adapted to mount the base body to the patient table, wherein the base body comprises:

an adjustable and lockable head-holder interface at the base body, which is adapted to adjustably couple the head-holder to the base body by providing at least three degrees of freedom for the spatial relative position between the head-holder and the base body, wherein the at least three degrees of freedom are lockable so as to establish a rigid coupling between the head-holder and the base body; and at least one robotic arm interface at the base body, which is adapted to provide a rigid coupling between a robotic arm and the base body.

In other words, the inventive head-holder support provides a self-contained unit which is on the one hand attachable to a surgical table for the patient, and on the other hand directly supports both, the head-holder for the patient and a robotic or semi-robotic support arm which aids in performing the medical procedure.

Put differently again, the head-holder support, or to be more precise the base body thereof, supports the head-holder and the robotic arm in a parallel fashion and transfers the forces and moments that are applied by these components onto the base body directly into the patient's table.

While the inventive head-holder support is small and therefore easy and flexibly to handle by medical personnel, it provides a most rigid connection between the head-holder and a robotic arm, as the number of intermediate structural components is reduced to the absolute minimum, with the base body being the only structural component between the interfaces for attaching the head-holder on the one hand, and the robotic arm on the other hand. The present invention therefore ensures that the spatial position between the robotic arm and the head-holder is securely maintained.

In a more specific example of the present invention, the base body is specifically developed to provide a stiff and stable connection between the robotic arm and the head-holder, wherein the material the base body comprises or consists of, as well as how such material is processed to form the base body may be chosen with the specific focus on rigidity. Regarding the head-holder interface, the aim of choosing the material the head-holder interface comprises or consists of as well as the production process to form the head-holder interface from this material may be a high radiolucency of the head-holder interface, since it may in some cases be desirable to produce images of the patient's head from time to time during a medical procedure to check whether the procedure develops as desired. As this may require to slide the patient's head into the gantry of a CT-imaging device, with the head-holder still engaging the patient's head, it becomes apparent that in such cases the head-holder interface desirably does not have negative impact on the imaging method performed with the CT-device.

Consequently, the head-holder interface may comprise or consist of a material that has a higher radiolucency than the material of the base body or even any other component of the inventive head-holder support. In a specific example, the head-holder interface may comprise or consist of a fiber reinforced plastic composite.

In a further example, the mounting device is adapted to mount the base body to an end of the patient table, particularly wherein the base body is substantially disposed below the upper plane of the patient table. In this example, the head-holder support is adapted to fit to the head-end of a conventional patient table known in the art. The mounting device may therefore include any conceivable means that allow the head-holder support to be mounted to such patient table, for example via a form-fit or a friction-fit provided by suitable elements such as clamps, screws or similar means.

Further, the head-holder support and in particular the mounting device can be formed such that the head-holder support, when mounted to the patient table, does not reach above the upper plane of the patient table. As a result, the patient may rest on the patient table, with the head and at least a substantial portion of the shoulder area reaching beyond the edge of the table's head-end, such that the patients head is freely accessible as it is engaged by the head-holder at a substantial distance from the table.

More specifically, the mounting device may be adapted to receive two rails disposed on opposite sides of the patient table. As these side-rails are very common on known patient tables, they may form a welcome possibility to mount the inventive head-holder support to the patient table. For this purpose, the mounting device may be adapted to receive such rails, for example by sliding over the respective ends thereof. Further, the rails may be held within the mounting device via a friction fit that could be applied by a clamping mechanism of the mounting device.

For example, the mounting device may comprise two separate brackets, one for each side-rail of the table, which are received by the base body in opposite directions and in particular perpendicularly to the direction the rails extend in. In this case, the brackets are automatically held in place at the base body as soon as they are attached to the corresponding side-rails, such that no additional means are necessary to secure the brackets to the base body. On the other hand, sliding these brackets into the base body in opposite directions allows them to engage side-rails of different types of tables for which the side-rails are provided at different distances. In any case, the brackets may of course be secured to the base body, for example by clamps, screws or similar means.

While in the above lines described a "universally fitting" head-holder support, which is intended to fit to a large number of patient tables, for example by providing different sets of mounting devices, particularly mounting brackets designed to fit to different types of patient tables, the inventive head-holder support may be specifically designed to form a part or a component of a so-called system table.

Such system tables are composed of table components which are interchangeably fitted to each other, such that different specific requirements for the table are met by adding or forming the whole table from system components which are suitable to meet the set requirements, while the remaining table components may remain the same. In this context, the inventive head-holder support may comprise a specific system-table interface for mounting the head-holder support to a system-table.

In a further example, the head-holder support comprises or forms part of a patient support surface. While in the case of a "universally fitting" head-holder support the base body may have an even upper surface a patient can comfortably rest on, a head-holder support designed for a system-table may form part of any conceivable system component of such system-table. For example, the table surface itself or a substantial part thereof may comprise the inventive head-holder support or may at least comprise a mounting interface the head-holder support can be attached to.

In order to allow positioning of the patient with the patient's head reaching a substantial amount over the head-end of the table, it is not possible for the head-holder support, specifically the base body, to reach above the upper table plane. Otherwise, the patient cannot comfortably rest on the table. However, this requires that the head-holder support, particularly the base body extends below the upper table plane to a certain extent such that the base body can provide a stable and secure structure between the interfaces for the robotic arm and the head-holder. As already described further above, it may in some cases be desirable to move the patient into an imaging device, for example a CT-imaging device, while the patient's head is still coupled via the head-holder and the inventive head-holder support to the patient table. Since it is desirable to position the patient's head in the center of a CT-gantry, the remaining space provided by the circular CT-gantry for the patient table and the head-holder support beneath the upper plane of the patient table is rather limited. Thus, the base body of the inventive head-holder support may taper below the upper plane of the patient table in a downward direction. By doing so, the available space between the upper plane of the patient table and the circular CT-gantry can be exploited to its maximum for the benefit of a base body construction which is as stable and stiff as possible.

Coming back to the head-holder interface, it is necessary for a head-holder to be at least to some degree freely positionable with respect to the patient table. The head-holder interface according to the present invention provides at least three degrees of freedom, and it can therefore comprise at least one section directly or indirectly coupled to the base member via at least one first joint and/or directly or indirectly coupled to the head-holder via at least one second joint. In other words, the head-holder interface may comprise at least one intermediate structure between the base body and the head-holder, which is connected therebetween via joints that can provide the aforementioned degrees of freedom. Anyone of the joints may provide at least one rotational and/or at least one translational degree of freedom, wherein any of these degrees of freedom may of course also be lockable so as to establish a rigid coupling between the head-holder and the base body.

In a further example, the head-holder interface comprises two or more sequentially arranged sections which of course can be connected to each other via joints as mentioned above. In such case, the joints may provide different degrees of freedom and may, of course, be lockable.

In regards to the at least one interface for a robotic arm, it is to be said that such interface(s) may be formed by the base body as a slotted clamp, such that a bottom section of the robotic arm is received and retained therein via a friction fit. In this context, the head-holder support can comprise two interfaces for a robotic arm disposed on opposite sides of the base body and/or the head-holder interface. Thus, the inventive head-holder support allows to position a robotic arm on either side of the patient's head, such that a maximum in accessibility of the patient's head for at least one robotic arm is reached.

In a further example, the head-holder support can accommodate, particularly on or within the base body, at least one of the following:
  a power supply unit for providing the robotic arm with electric energy;
  a control unit for receiving signals from and/or transmitting signals to at least one electric motor and/or at least one electromagnetic brake of the robotic arm, wherein the head-holder support further comprises at least one connection for transmitting the electric energy and/or the signals to and/or from the robotic arm.

BRIEF DESCRIPTION OF THE DRAWINGS

In the following, the invention is described with reference to the appended Figures which give background information and represent specific embodiment of the invention. The scope of the invention is however not limited to the specific features disclosed in the context of the Figures, wherein.

DESCRIPTION OF EMBODIMENTS

Figure 1:
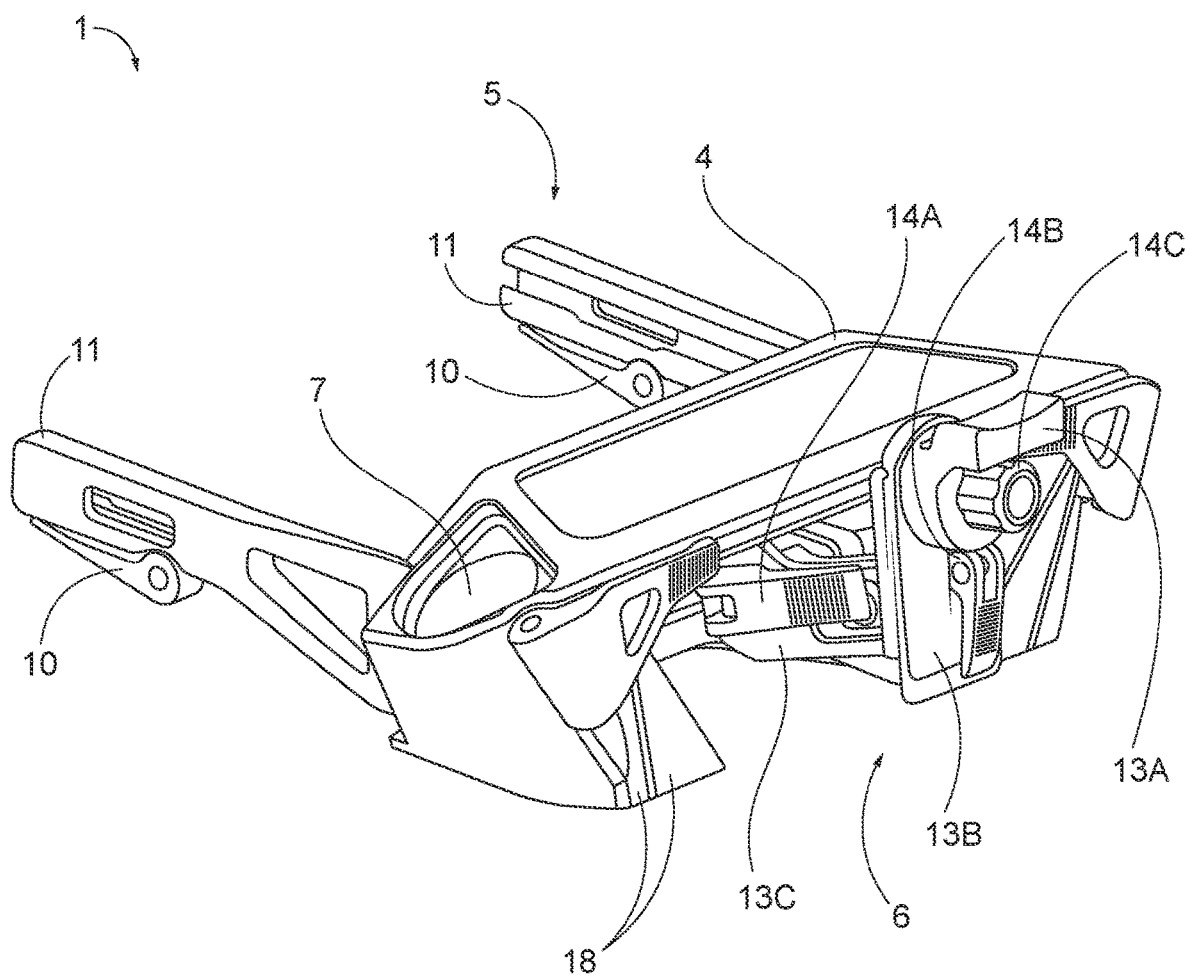
FIG. 1 shows a head-holder support according to the present invention.
Figure 5:
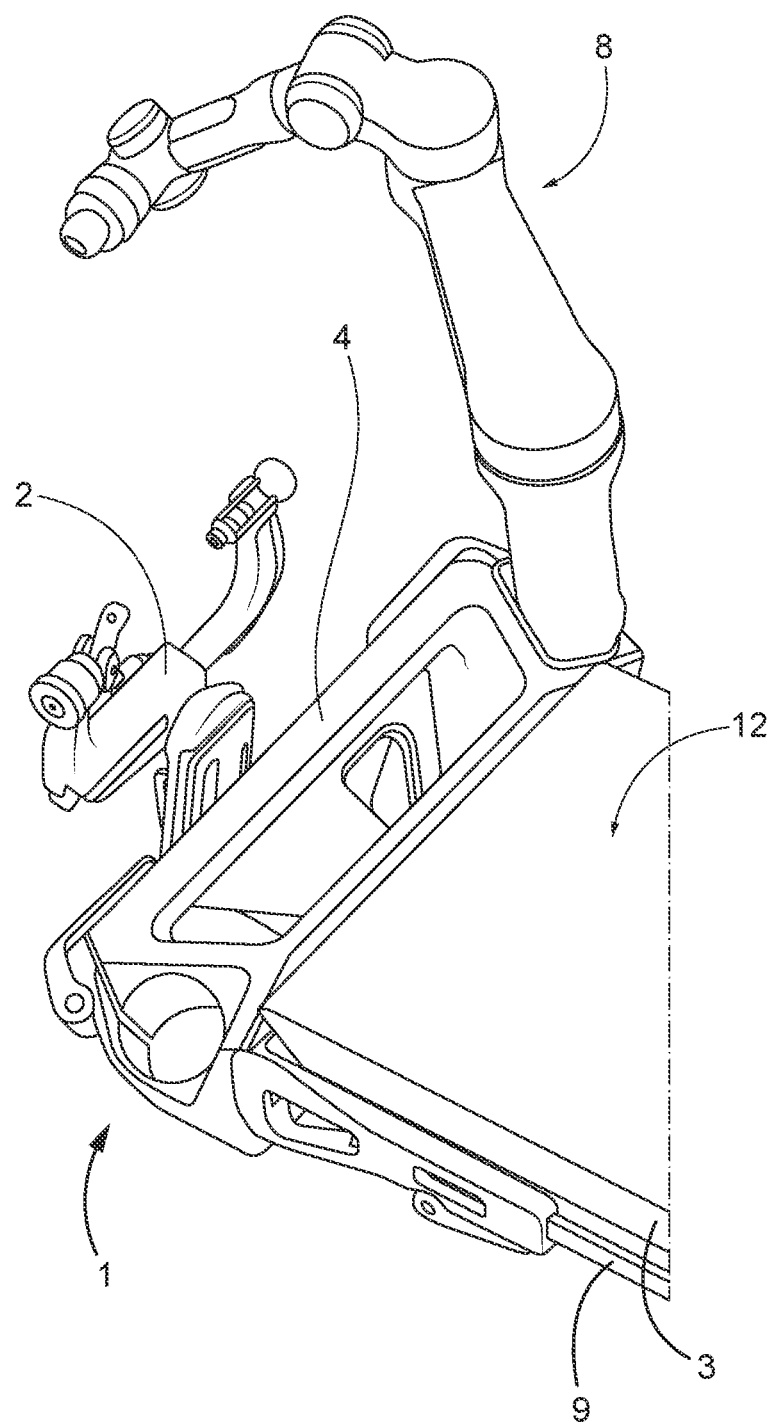
FIG. 5 shows the head-holder support of FIG. 1 with a head-holder and a robotic arm installed.

FIG. 1 shows an embodiment of the inventive head-holder support 1 with the central component thereof being the base body 4. The base body 4 forms two cup-shaped interfaces 7 that are specifically designed to receive and retain a correspondingly shaped bottom section of a robotic arm 8 (FIG. 5). While an upper section of the interface 7 is specifically shaped to receive a collar of the robotic arm 8, thereby defining an actual position of the robotic arm 8 with respect to the base body 4, the cup-shaped interfaces 7 further comprise a slot such that the interface 7 are formed as clamps 18 which retain a robotic arm 8 in at least the axial direction by a friction fit. The receptacles for the robotic arm's 8 collar are further shaped to define the rotational degree of freedom of the robotic arm 8 within the interface 7 since both, the receptacle and the collar have corresponding shapes which are not rotationally symmetrical. As soon as the bottom section of the robotic arm 8 is received within the interface 7 with its collar abutting the interface's 7 receptacle, the lever of the interface 7 can be closed, thereby moving the sections of the clamps 18 together, such that the robotic arm 8 is retained within the interface 7 via a friction fit.

Further, the head-holder support 1 comprises an interface 6 for a head-holder 2 (FIG. 5) between the two interfaces 7 and extending from a lower portion of the base body 4. The interface 6 comprises three sequentially arranged intermediate sections 13A to 13C, which are connected to each other and to the base body 4 via three lockable joints 14A to 14C. While joints 14A and 14B can be locked via a lever, joint 14C is locked via a locking screw 14C.

On the other end of the base body 4, opposite to the interface 6, the inventive head-holder support 1 comprises a mounting device 5 with two separate brackets 11 that extend from the base body 4 and are adapted to receive correspondingly formed side-rails 9 (FIG. 5) of a patient table 3 (FIG. 5). As soon as the corresponding rails 9 are received within the brackets 11, the head-holder support 1 can be secured through the patient table 3 by closing the levers 10 such that the rails 9 are maintained within the brackets 11 by a friction fit.

Figure 2:
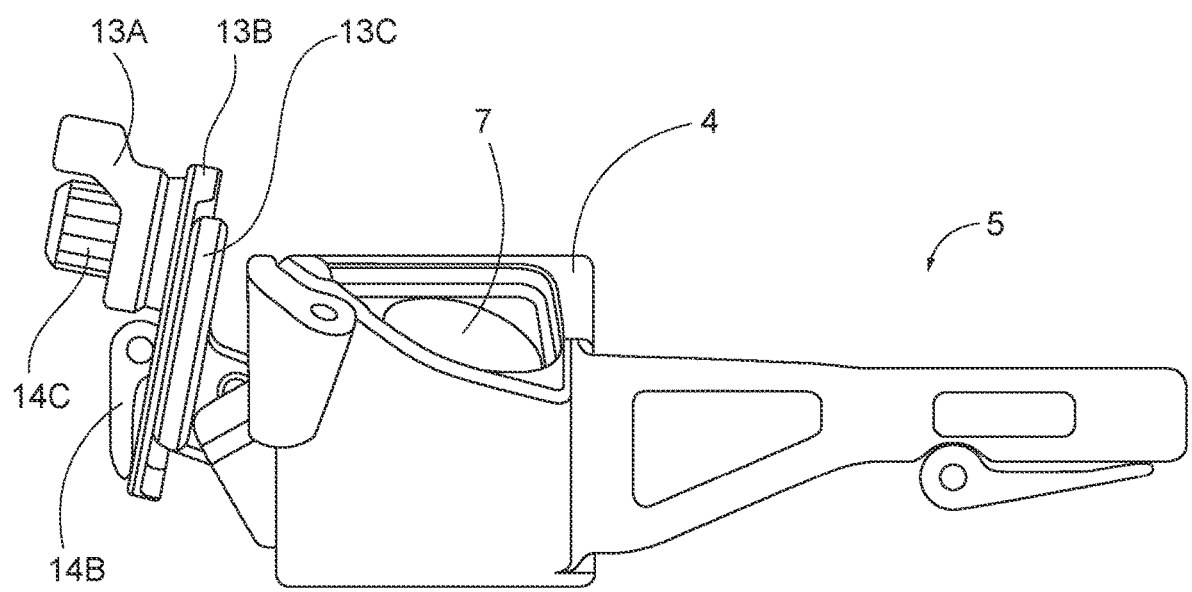
FIG. 2 shows a side-view of the head-holder of FIG. 1.
Figure 3:
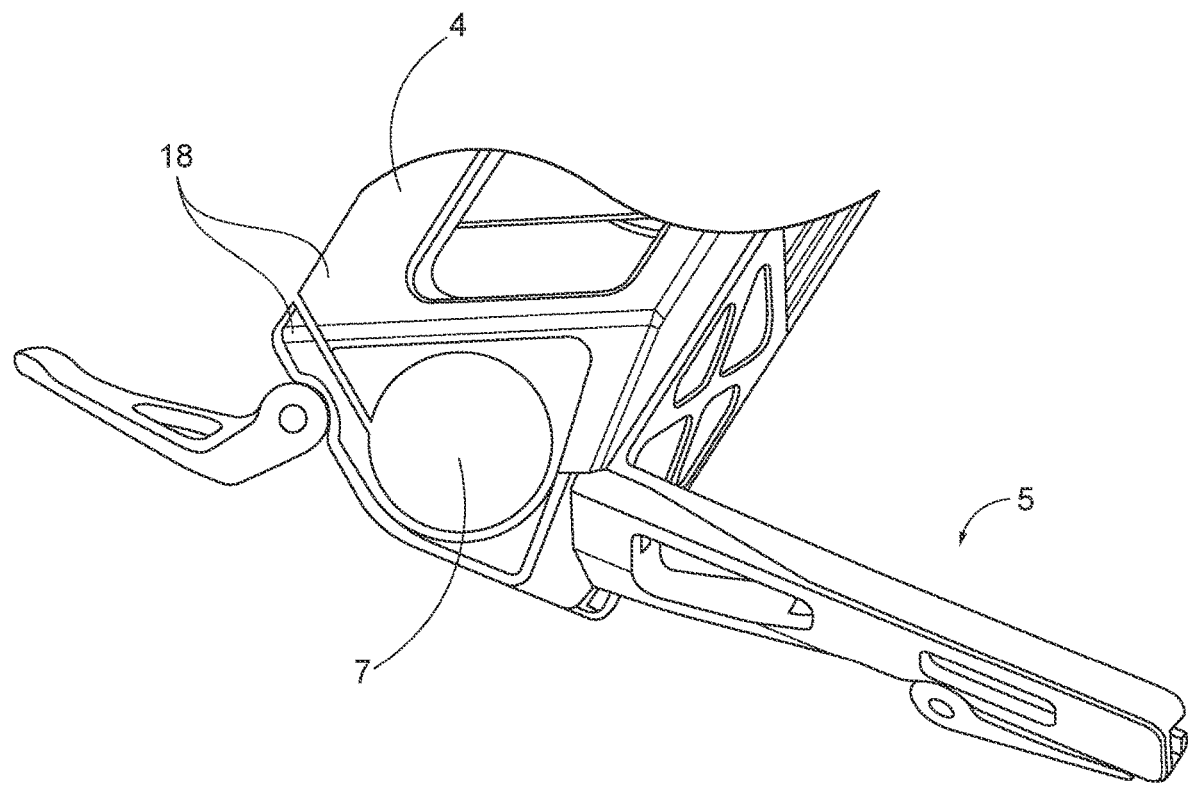
FIG. 3 shows a detailed view on the robotic arm interface of the head-holder support of FIG. 1.

As FIGS. 1 to 3 show, the inventive head-holder support and the base body 4 thereof are in particular specifically designed to provide a stiff and stable connection between the interface 7 and the interface 6.

Figure 4:
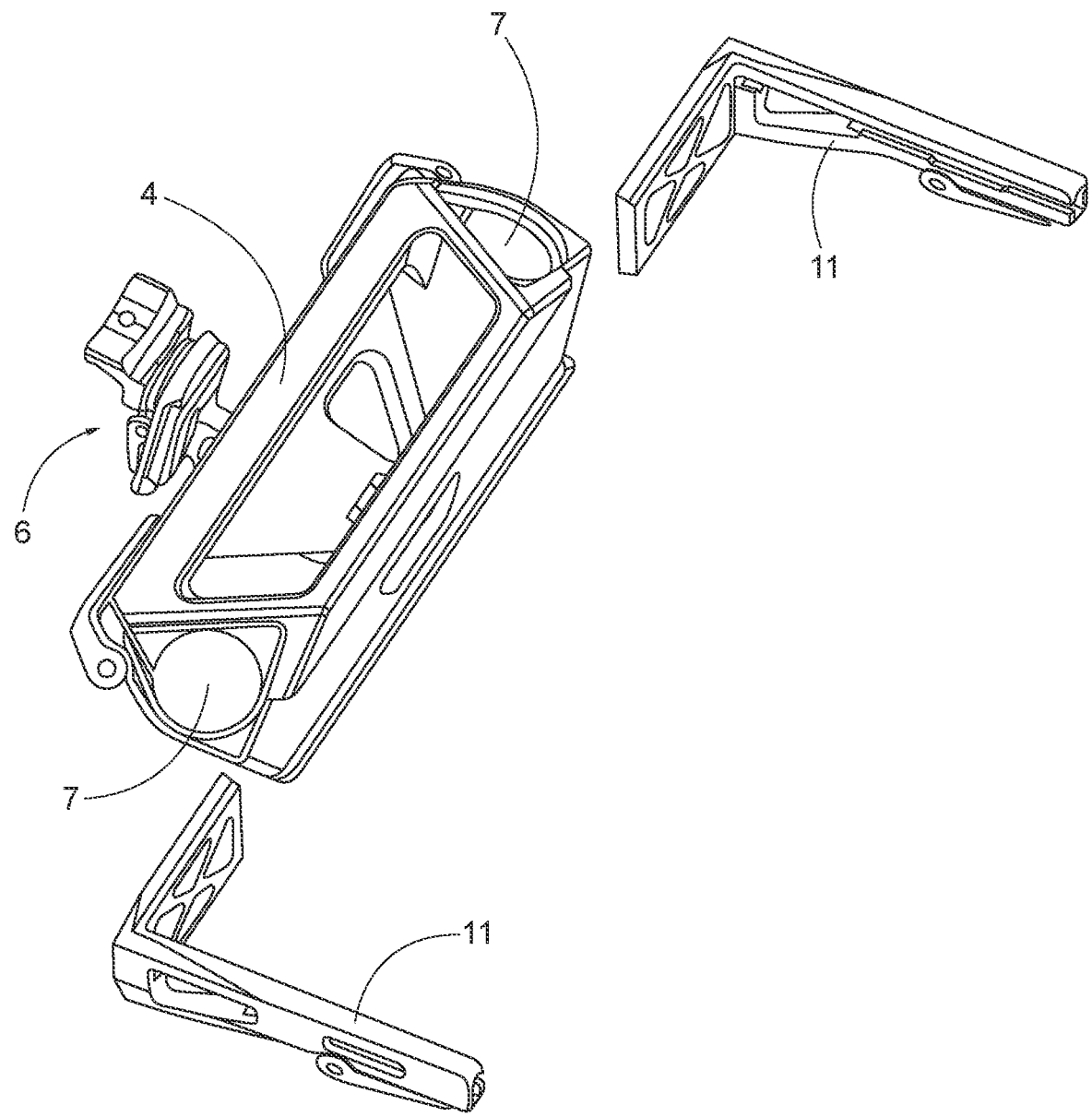
FIG. 4 shows the head-holder support of FIG. 1 with the mounting brackets detached.

As FIGS. 3 and 4 show, the brackets 11 of the mounting device 5 are removably connected to the base body 4 via a rail guide that extends perpendicular to the longitudinal receptacles in the brackets 11 for the side-rails 9

FIG. 5 shows the inventive head-holder support 1 being attached to a patient table 3, wherein the brackets 11 each receive a corresponding side-rail of the patient table 3. The base body 4 is thereby positioned at the head-end of the patient table 3, but does not reach above the upper plane 12 thereof.

Figure 6:
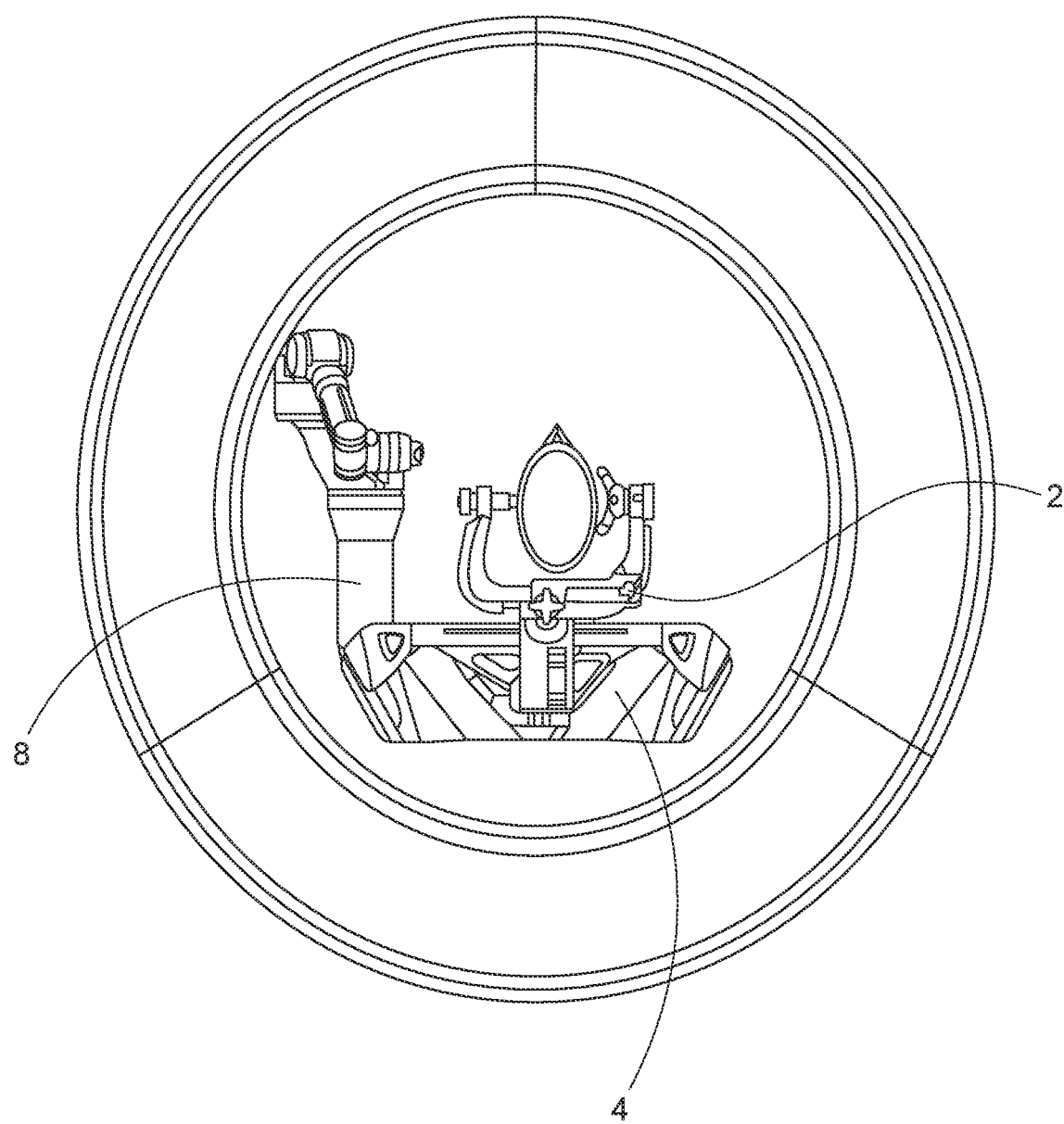
FIG. 6 shows a frontal view on the setup of FIG. 5 with respect to a CT-gantry.

For this reason, the base body 4 has a shape that is adapted to a circular gantry of a CT-device (FIG. 6; not indicated) such that, despite of the stable and stiff construction of the head-holder support, the patient table 3 together with the patient can still be positioned within the CT-gantry with the patient's head located in the center of the CT-gantry.

Figure 7:
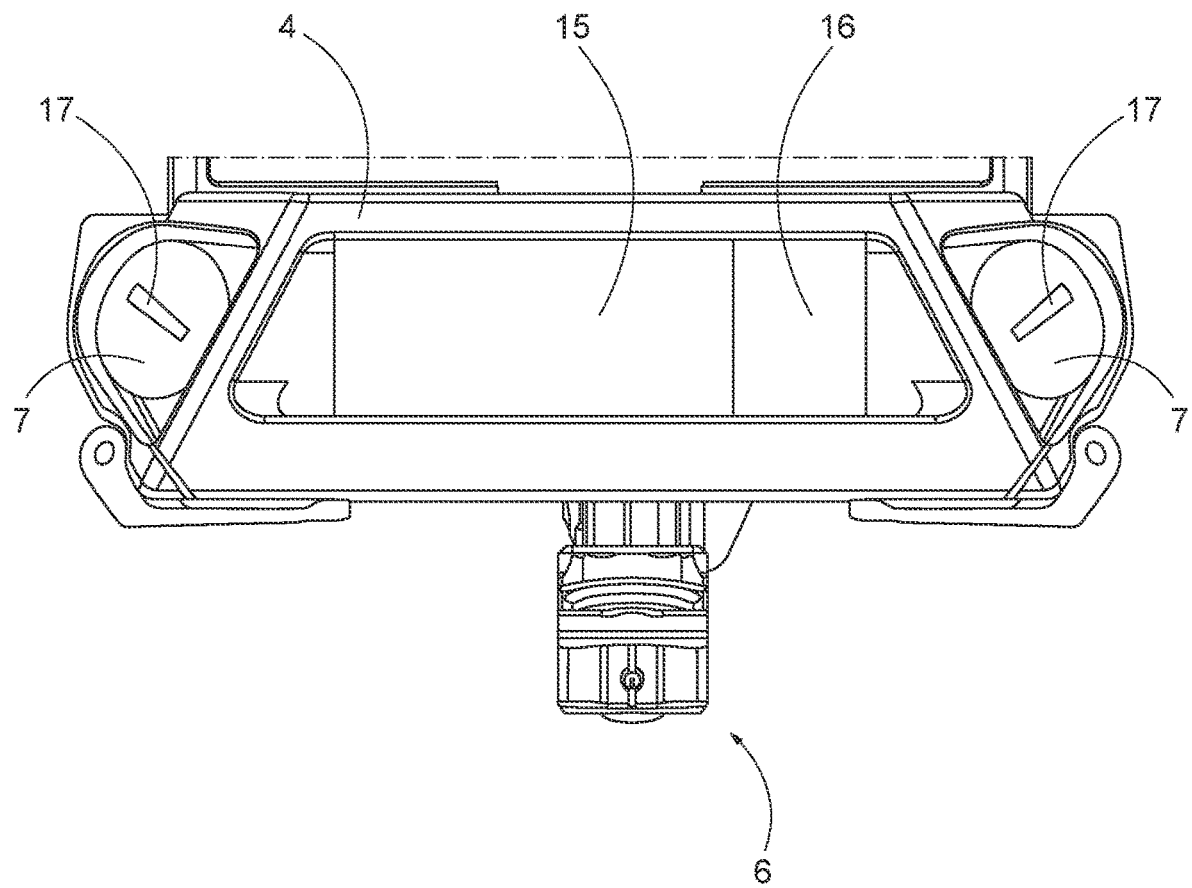
FIG. 7 shows the head-holder support of FIG. 1 with components for the robotic arm being integrated in the base body.

FIG. 7 shows a further example of the inventive head-holder support 1, wherein the base body 4 receives a power supply unit 15 and a control unit 16, both of which are assigned to the robotic arm 8, and which are connected thereto via a connection 17 within the cup-shaped interface 7. By disposing these electrical components at the base body 4, the heat dissipation of the robotic arm 8 itself is reduced to a minimum. As the robotic arm 8 is often positioned in the immediate vicinity to the patient's head, undesired heat input to the patient's anatomy can be successfully eliminated.

The invention claimed is:

1. A head-holder support for attaching a medical head-holder to a patient table, the head-holder support comprising:
    a rigid base body; and
    a mounting device having two separate brackets extending from the base body, wherein the two separate brackets are adapted to receive two correspondingly formed side-rails of the patient table for mounting the base body to the patient table,
    wherein the base body comprises:
        an adjustable and lockable head-holder interface at the base body, which is adapted to adjustably couple the head-holder to the base body by providing at least three degrees of freedom for a spatial relative position between the head-holder and the base body, wherein the at least three degrees of freedom are lockable so as to establish a rigid coupling between the head-holder and the base body; and
        at least one robotic arm interface at the base body, which is adapted to provide a rigid coupling between a robotic arm and the base body,
        wherein the base body represents a single structural component connecting between the head-holder interface and the at least one robotic arm interface for attaching the head-holder and the robotic arm, respectively.

2. The head-holder support according to claim 1, wherein the head-holder interface comprises a material having a higher radiolucency than a material of at least the base body.

3. The head-holder support according to claim 2, wherein the head-holder interface material comprises a fiber reinforced plastic composite.

4. The head-holder support according to claim 1, wherein the mounting device is adapted to mount the base body to an end of the patient table.

5. The head-holder support according to claim 4, wherein the patient table has an upper plane and a lower plane, and the base body is disposed below the upper plane of the patient table.

6. The head-holder support according to claim 5, wherein the head-holder support positions the head-holder at a position above and beyond the patient table such that a patient head is spaced from the table.

7. The head-holder support according to claim 1, wherein the two separate brackets are received by the base body in opposite directions and in particular perpendicularly to a direction of the two side-rails of the patient table.

8. The head-holder support according to claim 7, wherein the two separate brackets are adapted to engage a respective one of the two side-rails of the patient table at different distances.

9. The head-holder support according to claim 1, wherein the head-holder support forms part of a system table.

10. The head-holder support according to claim 1, wherein the head-holder support comprises or forms part of a patient support surface.

11. The head-holder support according to claim 1, wherein the head-holder interface comprises at least one section directly or indirectly coupled to the base body via at least one first joint and/or directly or indirectly coupled to the head-holder via at least one second joint.

12. The head-holder support according to claim 11, wherein the at least one joint provides at least one translational and/or at least one rotational degree of freedom.

13. The head-holder support according to claim 11, wherein the at least one joint comprises a locking mechanism by which it can be immobilized.

14. The head-holder support according to claim 11, wherein the head-holder interface comprises two or more sections, and wherein the two or more sections are arranged sequentially to adjustably couple the head-holder to the base body.

15. The head-holder support according to claim 1, wherein the head-holder interface disposes the head-holder at a position above and beyond the base body.

16. The head-holder support according to claim 1, wherein the robotic arm interface comprises a slotted clamp formed by the base body, which is adapted to receive and retain a section of the robotic arm via a friction fit.

17. The head-holder support according to claim 1, comprising an additional robotic arm interface, wherein the robotic arm interface and the additional robotic arm interface are disposed on opposite sides of the base body.

18. The head-holder support according to claim 1, wherein the head-holder support is adapted to receive at least one of the following:
    a power supply unit for providing the robotic arm with electric energy; and
    a control unit for receiving signals from and/or transmitting signals to at least one electric motor and/or at least one electromagnetic brake of the robotic arm;
    wherein the head-holder support further comprises at least one connection for transmitting the electric energy and/or the signals to and/or from the robotic arm.

19. A head-holder support for attaching a medical head-holder to a patient table, the head-holder support comprising:
    a rigid base body; and
    a mounting device having two separate brackets extending from the base body, wherein the two separate brackets are adapted to receive two correspondingly formed side-rails of the patient table for mounting the base body to the patient table,
    wherein the base body comprises:
        an adjustable and lockable head-holder interface at the base body, which is adapted to adjustably couple the head-holder to the base body and adapted to establish a rigid coupling between the head-holder and the base body; and
        at least one robotic arm interface at the base body, which is adapted to provide a rigid coupling between a robotic arm and the base body,
        wherein the base body represents a single structural component connecting between the head-holder interface and the at least one robotic arm interface for attaching the head-holder and the robotic arm, respectively.

* * * * *